US009005931B2

(12) United States Patent  
Sun et al.

(10) Patent No.: US 9,005,931 B2  
(45) Date of Patent: Apr. 14, 2015

(54) PROGRAMMABLE OLIGONUCLEOTIDE MICRO ARRAY

(75) Inventors: Zhenhong Sun, Shanghai (CN); Wendy Wang, Shanghai (CN); Hang Liao, Shanghai (CN)

(73) Assignee: Honeywell International Inc., Morristown, NJ (US)

( * ) Notice: Subject to any disclaimer, the term of this patent is extended or adjusted under 35 U.S.C. 154(b) by 261 days.

(21) Appl. No.: 12/810,078

(22) PCT Filed: Dec. 24, 2007

(86) PCT No.: PCT/CN2007/003754  
§ 371 (c)(1),  
(2), (4) Date: Sep. 15, 2010

(87) PCT Pub. No.: WO2009/079856  
PCT Pub. Date: Jul. 2, 2009

(65) Prior Publication Data  
US 2011/0015086 A1   Jan. 20, 2011

(51) Int. Cl.  
C12P 19/34 (2006.01)  
C12Q 1/68 (2006.01)  
B01L 7/00 (2006.01)

(52) U.S. Cl.  
CPC .............. *C12Q 1/6837* (2013.01); *C12Q 1/686* (2013.01); *B01L 7/52* (2013.01)

(58) Field of Classification Search  
None  
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,965,188 | A | 10/1990 | Mullis et al. |
| 2004/0091862 | A1 | 5/2004 | Brandenburg et al. |
| 2006/0088844 | A1* | 4/2006 | Xu .................................. 435/6 |

FOREIGN PATENT DOCUMENTS

| | | |
|---|---|---|
| WO | WO-93/06241 A1 | 4/1993 |
| WO | WO-2006/135437 A2 | 12/2006 |
| WO | WO-2009/059447 A1 | 5/2009 |

OTHER PUBLICATIONS

Francois et al. (2006) J of Microbiol. Methods vol. 65: pp. 390-403.*  
Rouillard et al. (2003) vol. 31, No. 12 pp. 3057-3062.*  
"European Application Serial No. 07855762.6, Amended Claims filed Jun. 22, 2010", 4 pgs.  
"International Application Serial No. PCT/CN2007/003754, International Search Report mailed Oct. 16, 2008", 2 pgs.  
"International Application Serial No. PCT/CN2007/003754, Written Opinion mailed Oct. 16, 2008", 5 pgs.  
Rouillard, J. M, et al., "OligoArray 2.0: design of oligonucleotide probes for DNA microarrays using a thermodynamic approach", *Nucleic Acids Research*, 31(12), (Jun. 15, 2003), 3057-3062.  
Von Ahsen, N., et al., "Oligonucleotide Melting Temperatures under PCR Conditions: Nearest-Neighbor corrections for $Mg^{2+}$, Deoxynucleotide Triphosphate, and Dimethyl Sulfoxide Concentrations with Comparison to Alternative Empirical Formulas", *Clin Chem.*, 47(11), (Nov. 2001), 1956-1961.  
"European Application Serial No. 07855762.6, Office Action mailed Oct. 5, 2011", 3 pgs.  
"European Application Serial No. 07855762.6, Response filed Feb. 3, 2012 to Office Action mailed Oct. 5, 2011", 7 pgs.  
"European Application Serial No. 07855762.6, Supplementary European Search Report mailed Sep. 14, 2011", 4 pgs.  
Francois, P., et al., "Rapid bacterial identification using evanescent-waveguide oligonucleotide microarray classifcation", *Journal of Microbiological Methods*, 65(3), (2006), 390-403.  
Stimpson, D. I. et al., "Real-time detection of DNA hybridization and melting on oligonucleotide arrays by using optical wave guides", *Proc. Natl. Acad. Sci. USA*, 92(14), (1995), 6379-6383.  
"International Application Serial No. PCT/CN2007/003754, International Preliminary Report on Patentability dated Jun. 29, 20", 6 pgs.  
"Chinese Application Serial No. 200780102357.9—Office Action Response", 10pgs.  
"Chinese Application Serial No. 200780102357.9, Office Action mailed Feb. 25, 2013", (w/ English Translation), 11 pgs.  
"Chinese Application Serial No. 200780102357.9, Office Acton mailed Jul. 3, 2013", 12 pgs.

* cited by examiner

*Primary Examiner* — Suchira Pande  
(74) *Attorney, Agent, or Firm* — Schwegman Lundberg & Woessner, P.A.

(57) ABSTRACT

A programmable probe design of DNA micro array and detection methodology is provided. DNA probes, which are complemented with the target DNA, are designed and classified into groups according to optimum hybridization temperature. The probes are arrayed by the group and immobilized on the substrate surface of the DNA micro array. The control system, imaging system and temperature control system are programmed to cooperate with each other during the detection process. This design increases the detection capabilities of the parallel-analysis system.

11 Claims, 11 Drawing Sheets

PROGRAMMABLE OLIGONUCLEOTIDE MICRO ARRAY

BACKGROUND OF THE INVENTION

The quantitative assay of nucleic acids is of considerable importance in basic biological research as well as in fields such as clinical microbiology. The real-time polymerase chain reaction (real-time PCR) process was developed in the mid 1990's to improve the original PCR process in a way that provides reliable, accurate quantitative measurements of the number of copies of any target DNA in the sample. In a real-time PCR, fluorogenic probes that are only active when bound to target DNA are added to the PCR buffer solution. These fluorogenic probes are single strands of DNA, with a middle portion having a sequence of nucleotides that is complementary to the target DNA. On either side of this middle portion, are extension nucleotide sequences that are complementary to each other, so that an unattached probe will fold onto itself in a hairpin configuration. The fluorogenic probe has a fluorescent molecule at one end, and a fluorescence quenching molecule at the other end. An unattached, folded probe has a fluorescing and a quenching molecule adjacent to each other, and consequently no fluorescent light is emitted when the unattached probe is illuminated. When the fluorogenic probe is attached to its target DNA, however, it is unfolded, with the fluorescing and quenching molecules separated from each other. When the attached probe is illuminated with the appropriate wavelength of light, the fluorescent molecule emits fluorescent light. By providing sufficient fluorogenic probes for a particular target DNA, and measuring the fluorescence from the bound probes at each stage of the PCR, the number of amplicons at each stage of the reaction can be measured. This measurement can be used to very accurately determine the number of copies of the DNA in the initial sample because of a straight line relationship between the fractional number of cycles for the number of amplicons to reach a pre-determined threshold and the logarithm of the number of copies in the initial sample.

BRIEF DESCRIPTION OF THE DRAWINGS

Embodiments of the invention may be best understood by referring to the following description and accompanying drawings, which illustrate such embodiments. In the drawings.

DEFINITIONS

Figure 1:
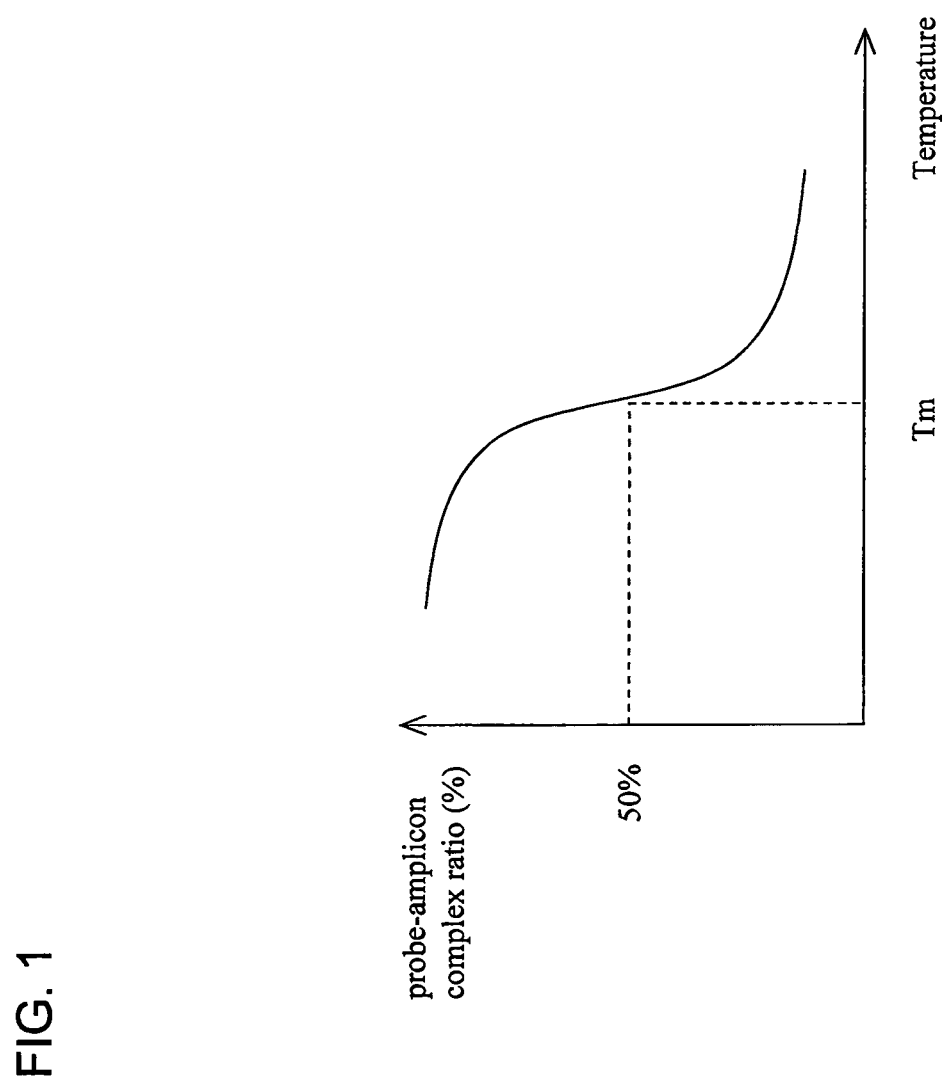
FIG. 1 illustrates a plot of melting temperature ($T_m$) versus probe-amplicon complex ratio.

As used herein, certain terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 11th Edition, by Sax and Lewis, Van Nostrand Reinhold, New York, N.Y., 1987, and *The Merck Index*, 11th Edition, Merck & Co., Rahway N.J. 1989.

As used herein, the term "and/or" means any one of the items, any combination of the items, or all of the items with which this term is associated.

As used herein, the singular forms "a," "an," and "the" may include plural reference unless the context clearly dictates otherwise. Therefore, for example, a reference to "a formulation" may include a plurality of such formulations, so that a formulation of compound X may include formulations of compound X.

As used herein, the term "about" means a variation of 10 percent of the value specified, for example, about 50 percent carries a variation from 45 to 55 percent. For integer ranges, the term about can include one or two integers greater than and less than a recited integer.

As used herein, the term "amplicons" refers to the products of polymerase chain reactions (PCR). Amplicons are pieces of DNA that have been synthesized using amplification techniques (e.g., a double-stranded DNA with two primers). The amplicon may contain, for example, a primer tagged with a fluorescent molecule at the 5' end.

As used herein, the terms "array" and "microarray" refer to an arrangement of elements (i.e., entities) into a material or device. In another sense, the term "array" refers to the orderly arrangement (e.g., rows and columns) of two or more assay regions on a substrate.

As used herein, the terms "complementary" or "complementarity" are used in reference to polynucleotides (i.e., a sequence of nucleotides) related by the base-pairing rules.

As used herein, the term "critical angle" is the angle of incidence above which the total internal reflection occurs.

As used herein, the term "evanescent" refers to a nearfield standing wave exhibiting exponential decay with distance. As used in optics, evanescent waves are formed when sinusoidal waves are internally reflected off an interface at an angle greater than the critical angle so that total internal reflection occurs.

As used herein, the term "hybridization" refers to the pairing of complementary nucleic acids.

As used herein, the term "$T_h$" refers to "hybridization temperature." The hybridization temperature is typically about 10° C. below the $T_m$ (melting temperature) of the nucleic acid.

As used herein, the term "nucleic acid molecule" refers to any nucleic acid containing molecule including, but not limited to, DNA or RNA. The term encompasses sequences that may include, for example, any of the known base analogs of DNA and RNA. As used herein, the term "polymerase chain reaction" (PCR) refers to the method of K. B. Mullis, U.S. Pat. Nos. 4,683,195, 4,683,202, and 4,965,188.

As used herein, the term "DNA polymerase" refers to a thermostable DNA polymerase enzyme having an optimum temperature at which it functions, which is higher than 40° C.

As used herein, the term "primer" refers to a single-stranded polynucleotide capable of acting as a point of initiation of template-directed DNA synthesis under appropriate conditions.

As used herein, the term "probe" refers to a nucleic acid capable of binding to a target nucleic acid of complementary sequence through one or more types of chemical bonds, usually through complementary base pairing, usually through hydrogen bond formation, thus forming a duplex structure. A probe binds or hybridizes to a "probe binding site." A probe can be labeled with a detectable label to permit facile detection of the probe, particularly once the probe has hybridized to its complementary target. A label attached to the probe can include any of a variety of different labels known in the art that can be detected by, for example, chemical or physical means. Labels that can be attached to probes may include, for example, fluorescent and luminescence materials. Probes can vary significantly in size. Some probes are relatively short. Generally, probes are at least 7 to 15 nucleotides in length. Other probes are at least 20, 30 or 40 nucleotides long. Still other probes are somewhat longer, being at least 50, 60, 70, 80, 90 nucleotides long. Yet other probes are longer still, and are at least 100, 150, 200 or more nucleotides long. Probes can be of any specific length that falls within the foregoing ranges as well.

As used herein, the term "substrate" refers to material capable of supporting associated assay components (e.g., assay regions, cells, test compounds, etc.). For example, in some embodiments, the substrate may include a planar (i.e., 2 dimensional) glass, metal, composite, plastic, silica, or other biocompatible or biologically unreactive (or biologically reactive) composition. The substrate is generally flat but may take on a variety of alternative surface configurations. The substrate and its surface are also chosen to provide appropriate light-absorbing characteristics. For instance, the substrate may be a polymerized Langmuir Blodgett film, a functionalized glass, a glass, quartz, Si, Ge, GaAs, GaP, $SiO_2$, $SiN_4$, modified silicon, or any one of a wide variety of gels or polymers, for example, (poly)tetrafluoroethylene, (poly)vinylidenedifluoride, polystyrene, polycarbonate, polyolefins such as polypropylene, or combinations thereof.

As used herein, the term "target nucleic acid" refers to a polynucleotide inherent to a pathogen that is to be detected. The polynucleotide is genetic material including, for example, DNA/RNA, mitochondrial DNA, rRNA, tRNA, mRNA, viral RNA, and plasmid DNA.

As used herein, the term "target nucleic acid probe" refers to a polynucleotide that is complementary to the target nucleic acid.

As used herein, the term "$T_m$" refers to the "melting temperature." The melting temperature is the temperature at which a population of double-stranded nucleic acid molecules becomes half dissociated into single strands. The equation for calculating the $T_m$ of nucleic acids is well known in the art (see, e.g., Anderson and Young, *Quantitative Filter Hybridization*, in Nucleic Acid Hybridization (1985)). For immobilized oligonucleotide probes, typically $T_m$, (° C.)=2 (number of adenosine and thymidine residues)+4 (number of guanosine and cytosine residues).

DETAILED DESCRIPTION OF THE INVENTION

The present invention provides a method, an apparatus, and a system capable of real-time, simultaneous, quantitative measurement of a plurality of target nucleic acids from one or more pathogens in a sample.

In one embodiment, the target nucleic acids in the sample are amplified using the polymerase chain reaction (PCR). The PCR is a well-known method of amplifying one or more stands of deoxyribonucleic acid (DNA). PCR is begun by placing the target nucleic acids in a buffer containing the nucleotides adenosine (ATP), thymidine (TTP), cytosine (CTP) and guanosine (GTP) (collectively referred to as dNTPs), a DNA polymerase, and primers. The primers are short strands of DNA, with sequences that complement the target nucleic acids to be amplified. The primers initiate replication of the target nucleic acids.

In one embodiment, the target nucleic acid primers may be fluorescently tagged with fluorescent molecules at the 5' end. In another embodiment, one of the target nucleic acid primers may be fluorescently tagged with fluorescent molecules at the 5' end. In yet another embodiment, the dNTPs are fluorescently tagged.

The PCR process has three main steps: denaturation, annealing, and extension. In the denaturation step, the mixture is heated to about 94° C. (Centigrade), at which point the target DNA separates into single strands. The mixture is quickly cooled. As the temperature falls to about 60° C., the annealing step occurs, in which the primers, which may be fluorescently tagged, hybridize or bind to their complementary sequences on the target nucleic acids. The extension step may be performed at about 60° C. or may be raised to the 72-78° C. range. In this step, the DNA polymerase uses the dNTPs in solution to extend the annealed primers, which may be fluorescently tagged, and forms new strands of DNA known as an amplicons. The mixture is briefly reheated back to about 94° C. to separate the newly created double helix stands into single strands of nucleic acid, which begins another cycle of the PCR process. With each cycle of the PCR process, the number of copies of the original target nucleic acids roughly doubles.

For real-time quantitative analysis of target nucleic acids, several methods utilizing evanescent wave detection techniques have been disclosed including, for example, the techniques described in Xu (U.S. Patent Application Publication No. 2006/0088844) and in PCT Patent Application Serial No. PCT/CN2007/003124, entitled "A QUANTITATIVE METHOD FOR OLIGONUCLEOTIDE MICROARRAY" filed Nov. 5, 2007.

In one embodiment, the PCR buffer additionally contains fluorescently tagged primers, that is, primers having a fluorescent dye molecule attached to them, so that upon completion of each PCR cycle, the amplicons produced are fluorescently tagged. The amplicons of the target nucleic acids are localized, using probe strands of DNA known as target nucleic acid probes. The target nucleic acid probes have the same complementary, nucleotide sequence as the target nucleic acids. The target nucleic acid probes are tethered to a substrate surface in a known, two-dimensional pattern, with the substrate surface forming part of the reaction cell containing the PCR ingredients.

During the annealing and extension phases of the PCR process, the target amplicons hybridize to their corresponding target nucleic acid probes. The hybridized, fluorescently tagged amplicons are illuminated with an evanescent wave of light of the appropriate wavelength to activate the fluorescent dye molecules of the fluorescently tagged primers or the fluorescently tagged dNTPs. This evanescent wave decays exponentially in power after entering the reaction cell via the substrate surface to which the target nucleic acid probes are tethered, with an effective penetration range of about 300 nm. This means that the evanescent wave penetrates far enough into the reaction cell to activate the fluorescently tagged amplicons hybridized to those target nucleic acid probes, but that it does not activate the fluorescently tagged molecules (e.g., the fluorescently tagged primers or the fluorescently tagged dNTPs) in solution in the main body of the reaction cell. By monitoring the strength of the fluorescence at various locations on the substrate surface, the current abundance of amplicons of the corresponding target nucleic acids can be determined. This may be done in real-time as the PCR progresses. The results are used to obtain a quantitative measure of the abundance of a specific target in the original sample, in a manner analogous to the real-time PCR calculation.

In another embodiment, the target nucleic acid probes are designed to be complementary to polynucleotides isolated from a pathogen selected from the group consisting of bacteria, viruses, fungi, and protozoa. In yet another embodiment, the target nucleic acid probes are designed to be complementary to a specific region of polynucleotides isolated from *Rickettsia*, *Chlamydia*, *Mycoplasma*, *Spirochete*, *Streptococcus*, *Salmonella*, *Staphylococcus*, *L. monocytogenes*, *N. meningitides*, *E. coli*, *H. influenzae*, *B. burgdorferi*, *Leptospira*, *Proteus*, *Anaerobacter*, *M. tuberculosis*, *Enterococcus*, *H. poliovirus* 1, *H. enterovirus* 71, *H. enterovirus* 70, *H. echovirus* 2, *H. echovirus* 4, *H. echovirus* 6, *H. echovirus* 9, *H. echovirus* 11, *H. echovirus* 12, *H. echovirus* 26, *H. coxsackievirus* A13, *H. coxsackievirus* A15, *H. coxsackievirus* A18, *H. coxsackievirus* A20, *H. coxsackievirus* A21, *H. coxsackievirus* B3-A, *H. coxsackievirus* B3-C, HSV-1, and HSV-2.

In one embodiment, the PCR utilizes probes including an oligonucleotide selected from the group consisting of SEQ ID NO: 1-9 (Table 1).

TABLE 1

| Species | Probe Sequence | Length | GC | AT | GC % | $T_m = (4 \times GC) + (2 \times AT)$ (° C.) | Theoretical $T_h = T_m - 15$ (° C.) | SEQ ID NO |
|---|---|---|---|---|---|---|---|---|
| *Staphylococcus* | TGACGGTACCTAATCAGAAAGCCAC | 25 | 12 | 13 | 0.48 | 74 | 59 | 1 |
| *Streptococcus* | GGTAACTAACCAGAAAGGGACGGC | 24 | 13 | 11 | 0.542 | 74 | 59 | 2 |
| *E. cloacae* | TGGTTAATAACCGCAGCAATTGACGT | 26 | 11 | 15 | 0.423 | 74 | 59 | 3 |
| *S. aureus* | TGTAAGTAACTGTGGACATCTTGACGG | 27 | 12 | 15 | 0.444 | 78 | 63 | 4 |
| *S. epidermidis* | TGTAAGTAACTATGGACGTCTTGACGG | 27 | 12 | 15 | 0.444 | 78 | 63 | 5 |
| *P. mirabilis* | AGGTGATAAGGTTAATACCCTTGTCAATT | 29 | 10 | 19 | 0.345 | 78 | 63 | 6 |
| *P. aeruginosa* | GAAGGGCAGTAAGTTAATACCTTGCTGTTT | 30 | 12 | 18 | 0.4 | 84 | 69 | 7 |
| *H. influenzae* | GTTGTAAAGTTCTTTCGGTATTGAGGAAGG | 30 | 12 | 18 | 0.4 | 84 | 69 | 8 |
| *E. coli* | GAAGGGAGTAAAGTTAATACCTTTGCTCATT | 31 | 11 | 20 | 0.355 | 84 | 69 | 9 |

The present invention also provides a method to increase the detection limit and specificity in an oligonucleotide microarray or a real-time PCR microarray.

In one embodiment, the probes for different target nucleic acids may be designed and classified into several groups. The probes in each group have approximately equivalent optimal hybridization temperatures. That is, each group of target nucleic acid probes may include one or more target nucleic acid probes with optimal hybridization temperatures within ten percent of each other; or within five percent of each other, or within three percent of each other, or within two percent of each other.

The probe sequences for each target molecule are designed and synthesized with conventional methods. Typically, one or more different probes are designed for each target molecule.

When the number of oligonucleotides is less than twenty, the melting temperature ($T_m$) of each probe may be calculated from formula $T_m$ (° C.)=2 (number of adenosine and thymidine residues)+4 (number of guanosine and cytosine residues). The probes in each group are arrayed on the substrate such that probes with a uniform hybridization temperature ($T_h$) are arrayed in a location such as a line. The melting temperature ($T_m$) represents the temperature at which 50% of the nucleic acid molecules are in double stranded form (e.g., a probe-amplicon complex).

The optimal hybridization temperature ($T_h$) is typically about 10-20° C. below the melting temperature ($T_m$) of the nucleic acid, which is influenced by strand length, base composition and chemical environment such as salt and formamide concentration. The optimal hybridization temperature ($T_h$) can be validated by hybridization kinetic analysis. The hybridization kinetic analysis for every probe may be performed, for example, in the following way. First, the corresponding target amplicons are hybridized with every probe at a series of different temperature for an appropriate length of time. With the decrease of hybridization temperature, more of the probe-amplicon complex will formed, as illustrated in FIG. 1. The hybridization temperature ($T_h$) represents the temperature, which satisfies a high specific hybridization signal, for example, the highest temperature at which 80% of the maximal signal is achieved. Second, the non-specific binding signal with other kinds of amplicons may not occur at this temperature. This may be validated with a certain concentration of other target amplicons and interfering amplicons, which not included in the target groups.

Usually a probe with high melting temperature ($T_m$) has a high hybridization temperature ($T_h$). The hybridization temperature ($T_h$) may be set as a function of the melting temperature ($T_m$), such as $T_h=T_m-15$. This may be validated and adjusted by the hybridization kinetic analysis.

To reduce the workload of hybridization temperature ($T_h$) validation and probe design, probes with similar melting temperature ($T_m$) can be chosen from the candidates to reduce the number. Those probes for high homologous target molecules can be designed in a low homologous region to increase their specificity.

In one embodiment, the DNA microarray is stationary and the optical detection system is mobile. The probes are arrayed by the group in the order of decreasing hybridization temperature ($T_h$) of each group and are immobilized on the substrate surface of the DNA microarray. After an appointed number of amplification cycles, the optical detection system is moved to the first group of probes. The chamber and the buffer solution containing the reagents are heated to the denaturing temperature of about 90° C. and maintained at this temperature for several seconds. The chamber and the buffer solution containing the reagents is cooled to the hybridization temperature for the first group of probes and maintained at this temperature for several seconds. The optical detection system measures the response of the first group of probes. Next, the optical detection system is moved to the second group of probes. The chamber and the buffer solution containing the reagents is cooled to the hybridization temperature for the second group of probes and maintained at this temperature for several seconds. For example, $T_{h1}>T_{h2}>T_{h3}$ is used because the probe groups with high hybridization temperature will be detected earlier at high temperature and the potential non-specific binding at $T_{h2}$ or $T_{h3}$ will not be detected and recorded. The optical detection system measures the response of the second group of probes. This cycle continues until all of the groups of probes have been detected. To optimize the reaction and detection efficiency, system parameters such as the number of amplification cycles before detection, the detection frequency (e.g., the number of amplification cycles between every detection cycle), temperature, time, rate of heating and cooling and movement of the optical detection system can be controlled by a computer program.

In another embodiment, the optical detection system is stationary and the DNA microarray is mobile. In another yet embodiment, both the optical detection system and the DNA microarray are mobile. Although $T_{h1}>T_{h2}>T_{h3}$ is used in the embodiments described above, in other embodiments $T_{h1}<T_{h2}<T_{h3}$ may be used.

Figure 2:
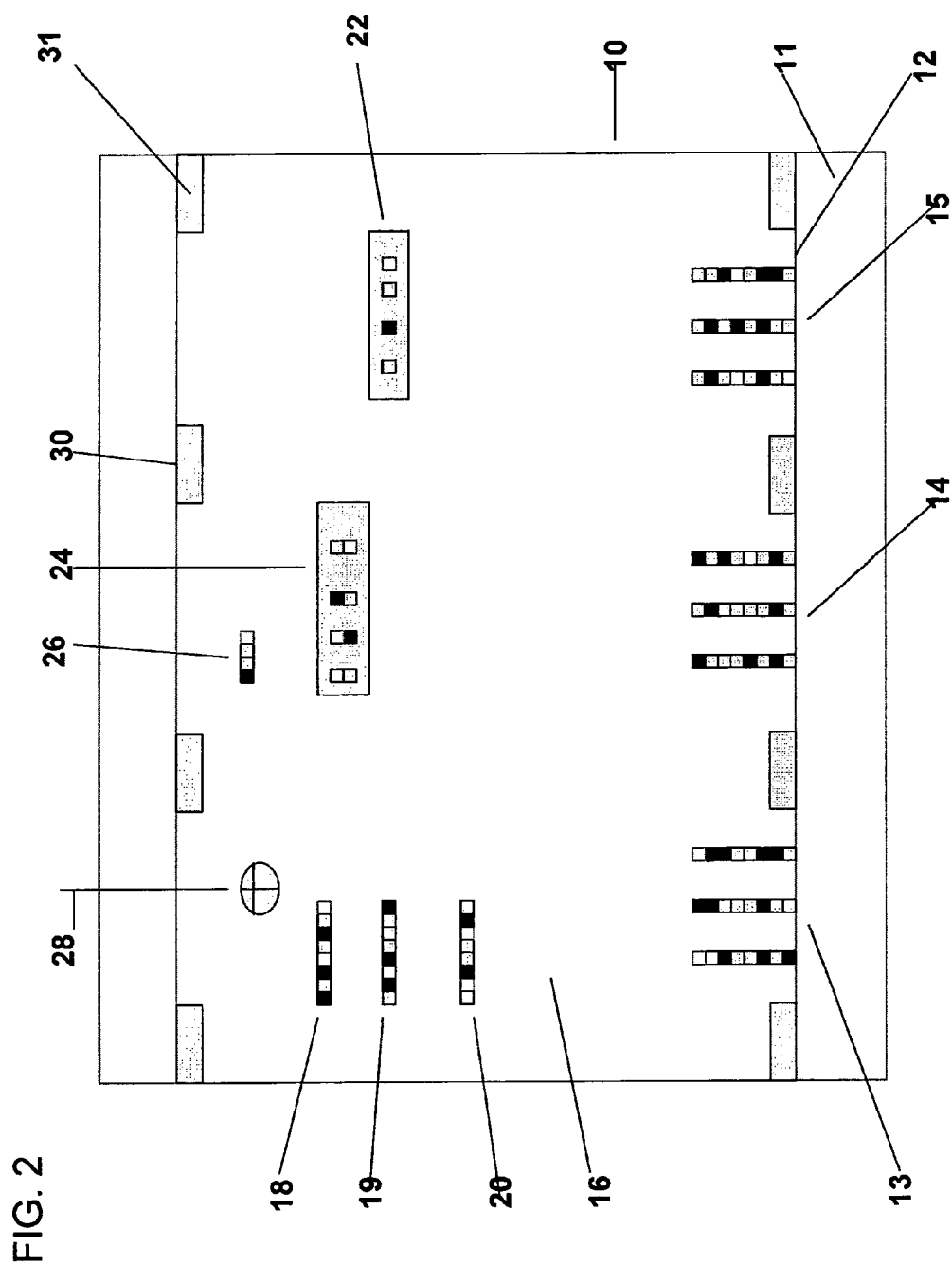
FIG. 2 illustrates a cross-sectional view of a cartridge capable of evanescent wave detection of fluorescently tagged amplicons in a microarrayed PCR process in an initial stage of the PCR process.

FIG. 2 is a cross-sectional view of a reaction cartridge capable of evanescent wave detection of fluorescently tagged amplicons in a microarrayed PCR process, including a reaction cartridge 10, a substrate 11 having a substrate surface 12, a first group of three target nucleic acid probes with hybridization temperature ($T_{h1}$) 13, a second group of three target nucleic acid probes with hybridization temperature ($T_{h2}$) 14, a third group of three target nucleic acid probes with hybridization temperature ($T_{h3}$) 15, wherein $T_{h1}>T_{h2}>T_{h3}$, a buffer solution 16, a first target nucleic acid strand 18, a second target nucleic acid strand 19, a third target nucleic acid strand 20, dNTPs 22, optional fluorescently tagged dNTPs 24, fluorescently tagged primers 26, a thermostable DNA polymerase 28, a heating element 30, and a cooling element 31. In some embodiments, the heating element 30 and cooling element 31 can be combined into one element, such as a semiconductor cooler, which could be used for either heating or cooling.

Although FIG. 2 illustrates three groups of three target nucleic acid probes, other combinations may be used such as two groups of two target nucleic acid probes, two groups of three target nucleic acid probes, three groups of two target nucleic acid probes, four groups of two target nucleic acid probes, four groups of three target nucleic acid probes, four groups of four target nucleic acid probes, and the like. In other words, there is not limit to the number of groups of target nucleic acid probes and the number of target nucleic acid probes within each group.

To simplify the drawings in FIG. 2-11, only one amplicon for one target nucleic acid probe each group is shown. However, it is to be understood that additional amplicons for other target nucleic acid probes within each group may be formed.

In one embodiment, the substrate 12 is comprised of a material that is optically denser than the buffer solution 16, so that evanescent wave detection can be used as described in detail below. The substrate 12 may for instance be glass, or a suitably coated plastic or polymer.

The first, second, and third groups of target nucleic acid probes 13, 14, and 15, respectively, each contain several strands of DNA, each strand of DNA having a specific nucleotide sequence of one of the target strands of DNA 18, 19, and 20 that they are used to detect, respectively. In one embodiment, these target nucleic acid probes are non-extendable. In other words, the nucleotides cannot be added to either end of the target nucleic acid probes. The target nucleic acid probes, which make up each group, may be natural or synthetically fabricated polynucleotides, polynucleotides with artificial bases and/or artificial carbohydrates, peptide nucleic acids (PNAs), bicyclic nucleic acids (BNAs), or other nucleotide analogs, constructed using a commercially available oligonucleotide synthesizer, for example, the POLYPLEX synthesizer available from Genomic Solutions, Inc. of Ann Arbor, Mich. Alternatively, the probes may be, but are not limited to, a sequence chosen from a library of DNA sequences, such as a library of expressed sequence tags (EST) known to have some biological significance.

The first, second, and third groups of target nucleic acid probes 13, 14, and 15, respectively, are arrayed on a substrate surface 12. In one embodiment, the probes that make up each group of target nucleic acid probes 13, 14, and 15 are arrayed on the substrate as small spots by robotic printing using commercially available microarraying technology, for example, the OMNIGRID microarrayer available from Genomic Solutions, Inc. of Ann Arbor, Mich.

The probes that make up each group of target nucleic acid probes 13, 14, and 15 may be immobilized on the substrate surface 12 by well-known techniques such as, but not limited to, covalently conjugating an active silyl moiety onto the target nucleic acid probes. Such silanized molecules are immobilized instantly onto glass surfaces after manual or automated deposition. Alternatively, the probes that make up each group of target nucleic acid probes 13, 14, and 15 may be immobilized by suitably electrically charging the surface, by using a suitable coating, for example, a silane, poly-L-lysine, streptavidin, a polysaccharide, mercaptan, or a combination thereof.

The fluorescently tagged primers 26 or the optionally fluorescently tagged dNTPs 24 are nucleotides that may be tagged with a fluorescent dye, for example, fluorescein or Rhodamine Green dyes, or similar, related compounds having similar fluorescing or luminescent characteristics, such as functionalized or intercalating dyes and luminescent, functionalized nanoparticles (quantum dots). The optionally fluorescently tagged dNTPs 24 may have one, two, three, or four of the four base nucleotides dGTP, dCTP, dATP, and dTTP that are fluorescently tagged.

Heating element 30 may be any suitable resistive material, for example, carbon, that provides heat when an electric current flows though it. Heating element 30 need to be capable of heating the reaction cartridge 10 to a temperature of 94° C. within minutes. Cooling element 31 may be any suitable solid state cooling element, for example, a well known Peltier solid-state device functioning as a heat pump. The heating element 30 and cooling element 31 can also be located outside the reaction cartridge 10. In some embodiments, the heating element 30 and cooling element 31 can be combined into one element, such as a semiconductor cooler, which could be used for either heating or cooling.

Figure 3:
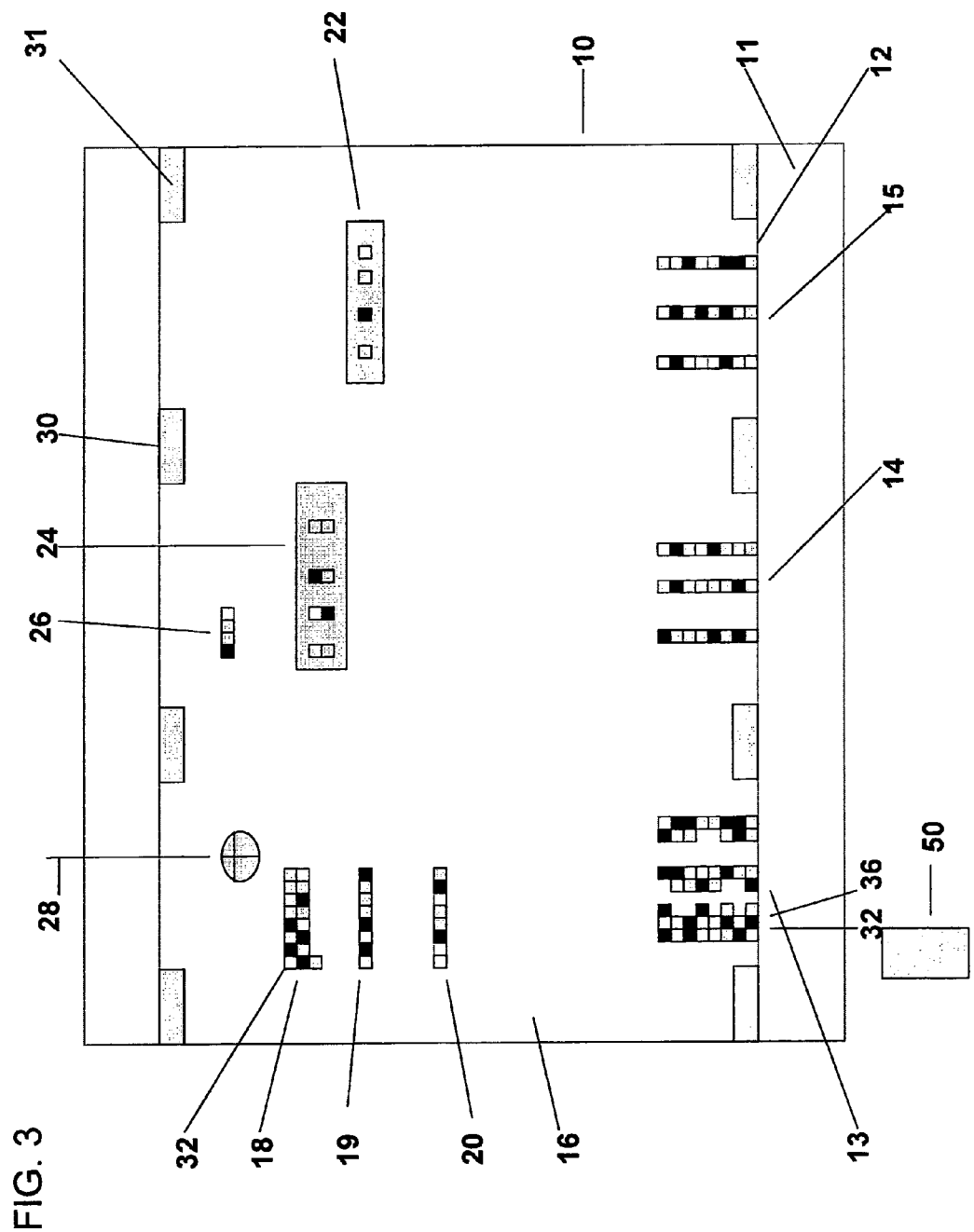
FIG. 3 illustrates a cross-sectional view of a cartridge capable of evanescent wave detection of fluorescently tagged amplicons in a microarrayed PCR process at the end of the annealing and extension stage using a hybridization temperature ($Th_1$) for the first group of target nucleic acids probes of the PCR process.

FIG. 3 is a cross-sectional view of a reaction cartridge 10 capable of evanescent wave detection of fluorescently tagged amplicons in a microarrayed PCR process using a hybridization temperature ($T_{h1}$) for the first group of target nucleic acids probes 13 of the PCR process, further including the first fluorescently tagged amplicon 32. The fluorescent light detector 50 is located adjacent to the substrate 12 to be able to monitor the PCR process of the first group of target nucleic acid probes 13.

First fluorescently tagged amplicon 32 is a DNA strand having a nucleotide sequence that is a complementary copy of one specific region of the first target nucleic acid strand 18, that is, for every adenosine (A) nucleotide in the one specific region of first target nucleic acid strand 18, there is a thymidine (T) nucleotide in the first fluorescently tagged amplicon 32, and vice versa. Similarly for every cytosine (C) nucleotide in the one specific region of first target nucleic acid strand 18, there is a guanosine (G) nucleotide in the one specific region of first fluorescently tagged amplicon 32. For example, if target strand 18 is 1000 base pairs (bp), the amplicon 32 may be, for example, 200 base pairs (bp) and the fragment for hybridization may be, for example, 20 base pairs (bp).

Using a hybridization temperature ($T_{h1}$) for the first group of target nucleic acids probes 13, first fluorescently tagged amplicon 32 will hybridize with the corresponding probes that make up the first group of target nucleic acid probes 13. For instance, at surface site 36, a first fluorescently tagged amplicon 32 is hybridized to a first target nucleic acid probe of group 13. However, there will still be hybridization taking place for the second and third set of nucleic acid probes 14 and 15 (with their corresponding amplicons respectively). For the second and third set of nucleic acid probes 14 and 15, their optimal hybridization temperature ($T_{h2}$) and ($T_{h3}$) is below ($T_{h1}$), so at ($T_{h1}$) their hybridization signal is less than their optimal hybridization signal.

The target nucleic acid probes that make up, for example, the groups 13, 14, and 15 are designed not to be amplified in the PCR process by, for instance, being tethered by their 3' end to the substrate, or by having the 3' end modified by dideoxidation or by having a stable group added to the 3' end or by any other well known methods of making the target nucleic acid probes not participate in a PCR process in the presence of specific primers.

Figure 4:
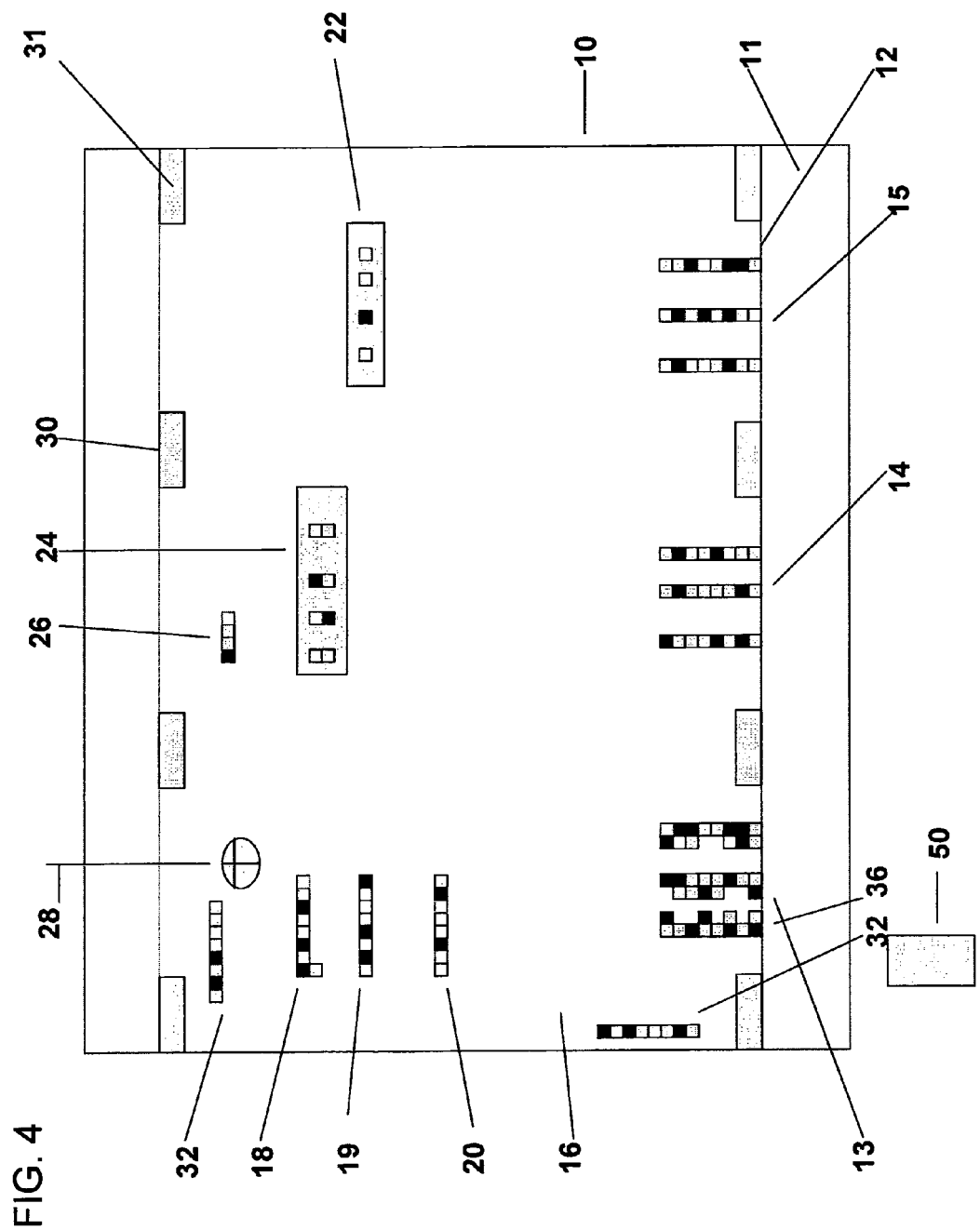
FIG. 4 illustrates a cross-sectional view of a cartridge capable of evanescent wave detection of fluorescently tagged amplicons in a microarrayed PCR process at the denaturation stage of the PCR process for the first group of target nucleic acids probes.

FIG. 4 is a cross-sectional view of a reaction cartridge 10 capable of evanescent wave detection of fluorescently tagged amplicons in a microarrayed PCR process at the denaturation stage of the PCR process. In this stage, the mixture within the reaction cartridge 10 has been heated to close to 100° C., and optimally to about 94° C. At this temperature, the DNA is denatured, that is, it separates into individual, single strands. When cooled to the hybridization temperature ($T_{h1}$) for the first group of target nucleic acids probes 13, the first target nucleic acid strand 18 as well as each of the first fluorescently tagged amplicon 32 will anneal with fluorescently tagged primers 26. The annealed fluorescently tagged primers 26 will be extended as the thermostable DNA polymerase 28 adds appropriate nucleotides, until the first target nucleic acid strand 18 and the first fluorescently tagged amplicon 32 will be hybridized to a new amplicon, which is a copy or a complementary copy of the original first target nucleic acid strand 18. Amplification may also take place during the detection cycle. As such, the detection cycle is conducted by, for example, programming the number of amplification cycles before detection and the detection frequency (e.g., the number of amplification cycles between every detection cycle).

Figure 5:
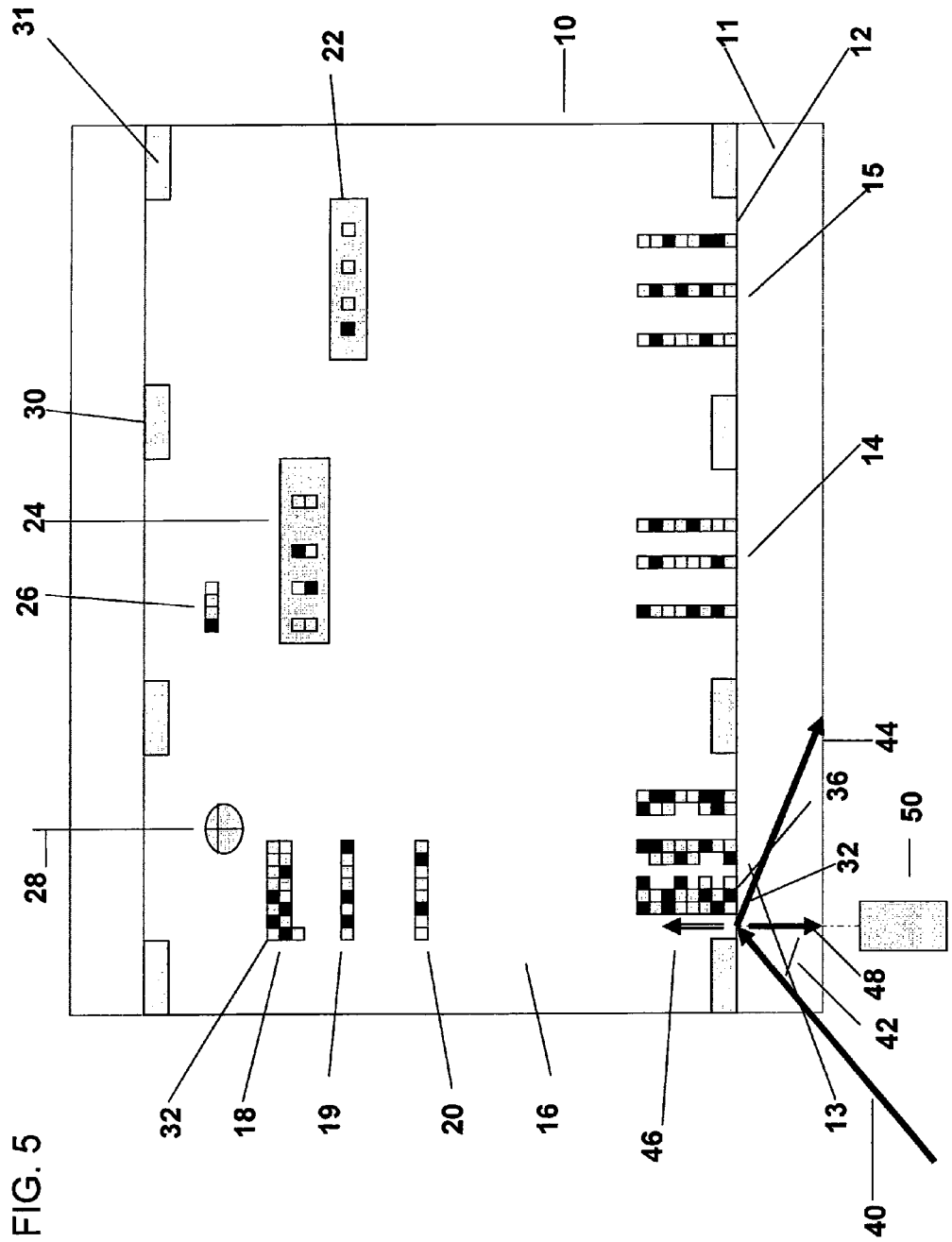
FIG. 5 illustrates a cross-sectional view of a cartridge showing evanescent wave detection of fluorescently tagged amplicons in a microarrayed PCR process at the detection stage of the PCR process for the first group of target nucleic acids probes.

FIG. 5 is cross-sectional view of a reaction cartridge 10 showing evanescent wave detection of fluorescently tagged amplicons in a microarrayed PCR process at the detection stage of the PCR process for the first group of nucleic acids probes 13, further including an incident beam of light 40, an angle of incidence 42, a reflected beam of light 44, an evanescent wave of light 46, a fluorescent beam of light 48 and a fluorescent light detector 50. The detection stage can be coincident with the annealing and/or extension stage.

The incident beam of light 40 is chosen to be of a wavelength suitable for exciting the fluorophore used to label the fluorescently tagged primers 16 or the optionally fluorescently tagged dNTPs 24. In one embodiment, the incident beam of light 40 is the 488 nm spectral line of an argon-ion laser, which closely matches the excitation maximum (494 nm) of fluorescein dye that is used to tag or label the fluorescently tagged primers 16 or the optionally fluorescently tagged dNTPs 24.

The angle of incidence 42 of the incident beam of light 40 is chosen to be greater than the critical angle of the substrate to buffer interface. The critical angle of incidence is the angle at which total internal reflection occurs and is dependent on the refractive indices of the materials forming the interface. From Snell's laws of refraction, the critical angle of incidence=$\sin^{-1}(n_1/n_2)$ where $n_1$ and $n_2$ are the refractive indices of the materials on either side of the interface. In one embodiment of the present invention, the substrate 12 is comprised of glass and has a refractive index of about 1.5, while the buffer solution 16 is comprised mainly of water having a refractive index of about 1.3, so that the critical angle of incidence is about 61 degrees.

When light is reflected off the substrate surface 12 at an angle of incidence 42 degrees greater than the critical angle so that total internal reflection occurs, an evanescent wave 46 is formed and propagates through the substrate surface 12. The intensity of the evanescent wave 46 drops by a factor of "e" (i.e., the mathematical constant) for each 130 nm increase in distance from the substrate surface 12. Therefore, only objects very near substrate surface 12 are illuminated by the evanescent wave 46. This property is used in one embodiment of the present invention to illuminate the first fluorescently tagged amplicon 32 that is hybridized to the first group of target nucleic acid probes 13. The fluorescent light 48 emitted by the fluorescently tagged amplicon 32, may be detected and analyzed by the fluorescent light detector 50. The fluorescent light detector 50 typically may include collection optics such as, a microscope objective lens, which focuses the light on to a detection system such as, a photomultiplier tube or a charge coupled device (CCD) camera or photodiodes.

The origin and intensity of the collected fluorescent light can be used to estimate the number of fluorescently emitting molecules and therefore the number of fluorescently tagged amplicons currently hybridized to a particular type of oligoprobe by using, for example, the well known quantification techniques employed in Real-Time or Kinetic PCR analysis. In the Real-Time or Kinetic PCR analysis, the reactions are characterized by the point in time during cycling when amplification of a PCR product is first detected, rather than the amount of PCR product accumulated after a fixed number of cycles. The greater the number of copies of a target nucleic acid in the initial sample, the sooner a significant increase in fluorescence is observed.

Figure 6:
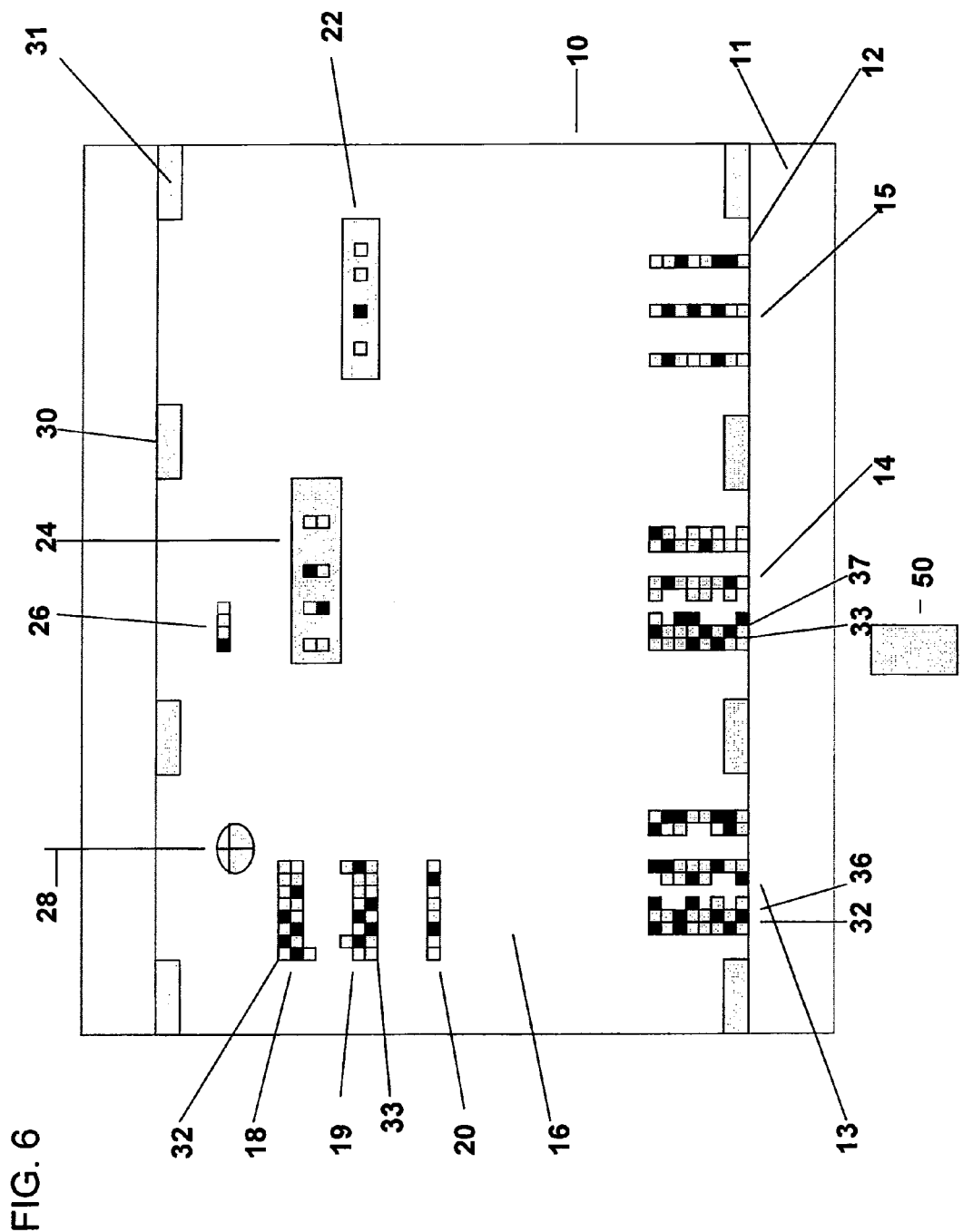
FIG. 6 illustrates a cross-sectional view of a reaction cartridge capable of evanescent wave detection of fluorescently tagged amplicons in a microarrayed PCR process at the end of the annealing and/or extension stage using hybridization temperature ($Th_2$) for the second group of target nucleic acids probes of the PCR process.

After the hybridization cycle is completed for the first group of target nucleic acid probes 13, the fluorescent light detector 50 is moved into position to monitor the second group of target nucleic acid probes 14 as shown in FIG. 6.

FIG. 6 is a cross-sectional view of a reaction cartridge 10 capable of evanescent wave detection of fluorescently tagged amplicons in a microarrayed PCR process at the end of the annealing and/or extension stage using a hybridization temperature ($T_{h2}$) for the second group of target nucleic acids probes 14 of the PCR process, further including the second fluorescently tagged amplicon 33.

Second fluorescently tagged amplicon 33 is a DNA strand having a nucleotide sequence that is a complementary copy of the second target nucleic acid strand 19, that is, for every adenosine (A) nucleotide in the second target nucleic acid strand 19, there is a thymidine (T) nucleotide in the second fluorescently tagged amplicon 33, and vice versa. Similarly for every cytosine (C) nucleotide in the second target nucleic acid strand 19, there is a guanosine (G) nucleotide in the second fluorescently tagged amplicon 33. For example, if target strand 19 is 1000 base pairs (bp), the amplicon 33 may be, for example, 200 base pairs (bp) and the fragment for hybridization may be, for example, 20 base pairs (bp).

At the end of the annealing and/or extension stage of the PCR process using a hybridization temperature ($T_{h2}$) for the second group of target nucleic acids probes 14, second fluorescently tagged amplicon 33 produced by extension of annealed fluorescently tagged primers 26, remains hybridized to its corresponding probes that make up the second group of target nucleic acid probes 14. Additionally, amplicons produced in previous cycles of the PCR process are hybridized to the tethered corresponding probes that make up the second group of target nucleic acid probes 14. For instance, at surface site 37, a second fluorescently tagged amplicon 33 is hybridized to a second target nucleic acid probe of group 14. However, there is no hybridization taking place for the third set of nucleic acid probes 15 because the hybridization temperature ($T_{h2}$) for the second group of target nucleic acids probes 14 for is below the hybridization temperature ($T_{h3}$) for the third group of target nucleic acids probes 15.

Figure 7:
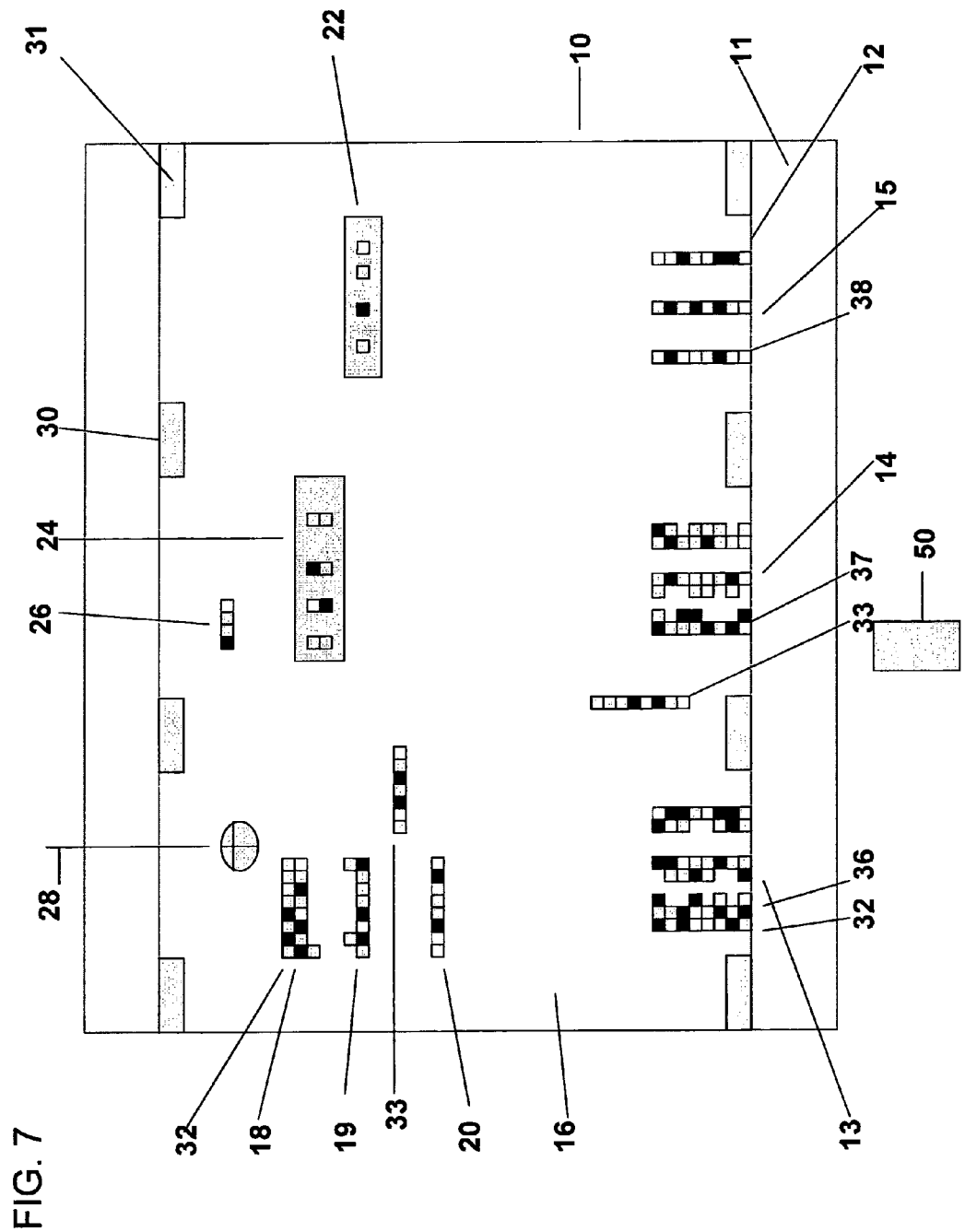
FIG. 7 illustrates a cross-sectional view of a reaction cartridge capable of evanescent wave detection of fluorescently tagged amplicons in a microarrayed PCR process at the denaturation stage of the PCR process for the second group of target nucleic acids probes.

FIG. 7 is a cross-sectional view of a reaction cartridge 10 capable of evanescent wave detection of fluorescently tagged amplicons in a microarrayed PCR process at the denaturation stage of the PCR process. In this stage, the mixture within the reaction cartridge 10 has been heated to close to 100° C., and optimally to about 94° C. At this temperature, the DNA is denatured, that is, it separates into individual, single strands. When cooled to the hybridization temperature ($T_{h2}$) for the second group of target nucleic acids probes 14 in the next stage of the PCR process, the second target nucleic acid strand 19 as well as each of the second fluorescently tagged amplicon 33 will anneal with fluorescently tagged primers 26. The annealed fluorescently tagged primers 26 will be extended as the thermostable DNA polymerase 28 adds appropriate nucleotides, until the second target nucleic acid strand 19 and the second fluorescently tagged amplicon 33 will be hybridized to a new amplicon, which is a copy or a complementary copy of the original second target nucleic acid strand 19. Amplification may also take place during the detection cycle. As such, the detection cycle is conducted by, for example, programming the number of amplification cycles before detection and the detection frequency (e.g., the number of amplification cycles between every detection cycle).

Figure 8:
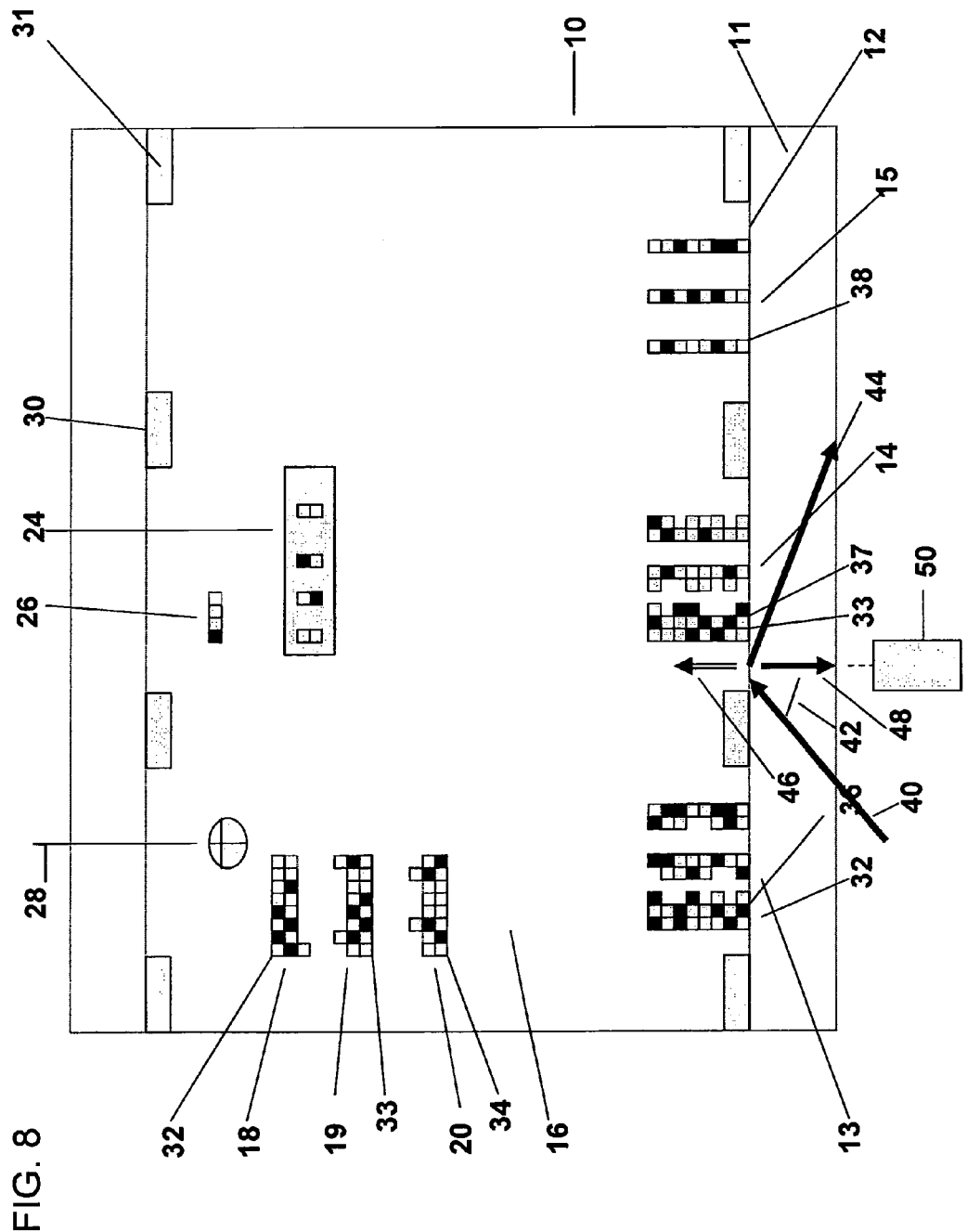
FIG. 8 illustrates cross-sectional view of a reaction cartridge showing evanescent wave detection of fluorescently tagged amplicons in a microarrayed PCR process at the detection stage of the PCR process for the second group of target nucleic acids probes.

FIG. 8 is cross-sectional view of a reaction cartridge 10 showing evanescent wave detection of fluorescently tagged amplicons in a microarrayed PCR process at the detection stage of the PCR process for the second group of target nucleic acids probes 14, further including an incident beam of light 40, an angle of incidence 42, a reflected beam of light 44, an evanescent wave of light 46, a fluorescent beam of light 48 and a fluorescent light detector 50. The detection stage can be coincident with the annealing and/or extension stage.

Figure 9:
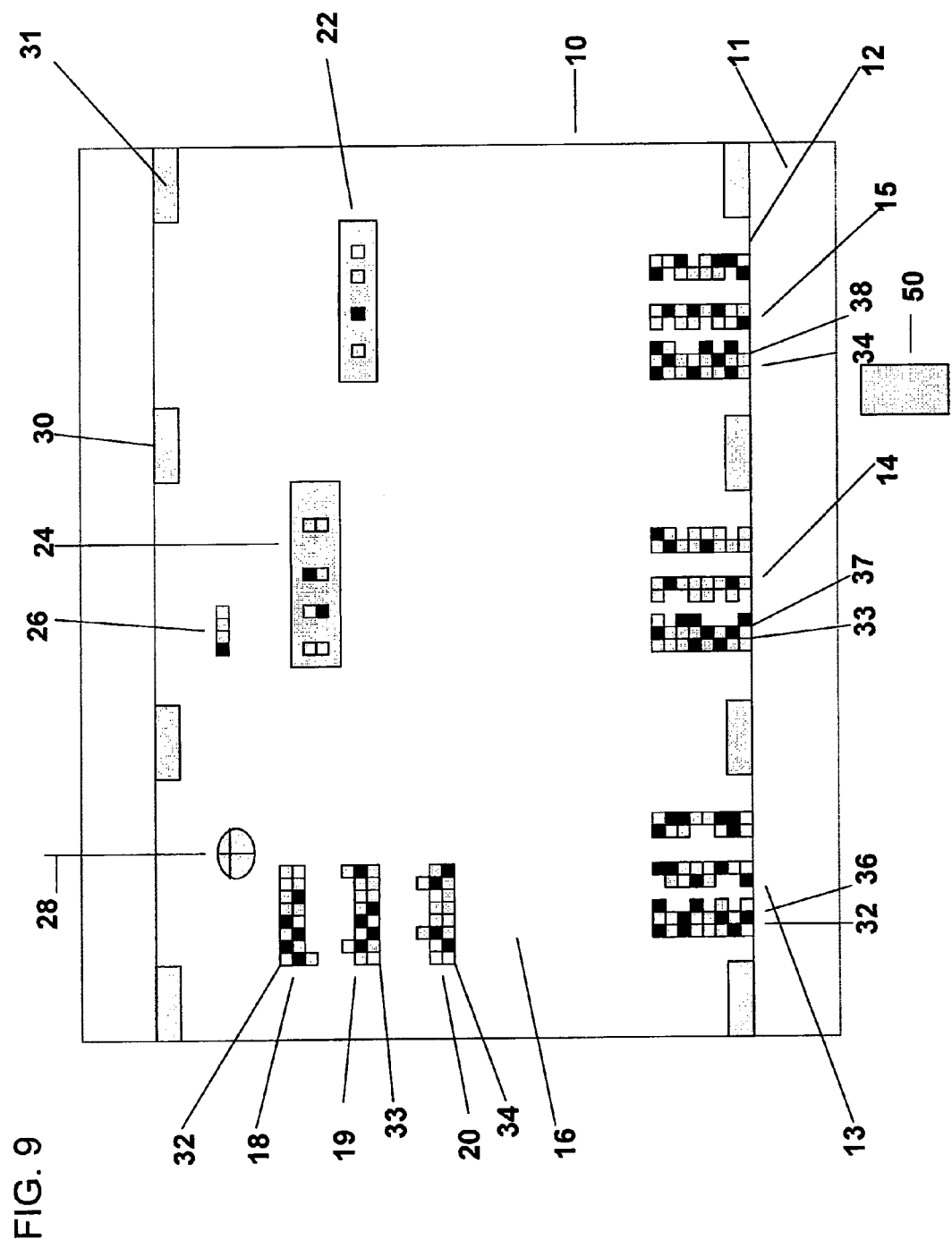
FIG. 9 illustrates a cross-sectional view of a reaction cartridge capable of evanescent wave detection of fluorescently tagged amplicons in a microarrayed PCR process at the end of the annealing and/or extension stage using hybridization temperature ($Th_3$) for the third group of target nucleic acids probes of the PCR process.

After the hybridization cycle is completed for the second group of target nucleic acid probes 14, the fluorescent light detector 50 is moved into position to monitor the third group of target nucleic acid probes 15 as shown in FIG. 9.

FIG. 9 is a cross-sectional view of a reaction cartridge 10 capable of evanescent wave detection of fluorescently tagged amplicons in a microarrayed PCR process at the end of the annealing and/or extension stage using a hybridization temperature ($T_{h3}$) for the third group of target nucleic acids probes 15 of the PCR process, further including the third fluorescently tagged amplicon 34.

Third fluorescently tagged amplicon 34 is a DNA strand having a nucleotide sequence that is a complementary copy of the third target nucleic acid strand 20, that is, for every adenosine (A) nucleotide in the third target nucleic acid strand 20, there is a thymidine (T) nucleotide in the third fluorescently tagged amplicon 34, and vice versa. Similarly for every cytosine (C) nucleotide in the third target nucleic acid strand 20, there is a guanosine (G) nucleotide in the third fluorescently tagged amplicon 34. For example, if target strand 20 is 1000 base pairs (bp), the amplicon 34 may be, for example, 200 base pairs (bp) and the fragment for hybridization may be, for example, 20 base pairs (bp).

At the end of the annealing and/or extension stage of the PCR process using a hybridization temperature ($T_{h3}$) for the third group of target nucleic acids probes 15, third fluorescently tagged amplicon 34 produced by extension of annealed fluorescently tagged primers 26, remains hybridized to its corresponding probes that make up the third group of target nucleic acid probes 15. Additionally, amplicons produced in previous cycles of the PCR process are hybridized to the tethered corresponding probes that make up the third group of target nucleic acid probes 15. For instance, at surface site 38, a third fluorescently tagged amplicon 38 is hybridized to a third target nucleic acid probe of group 15.

Figure 10:
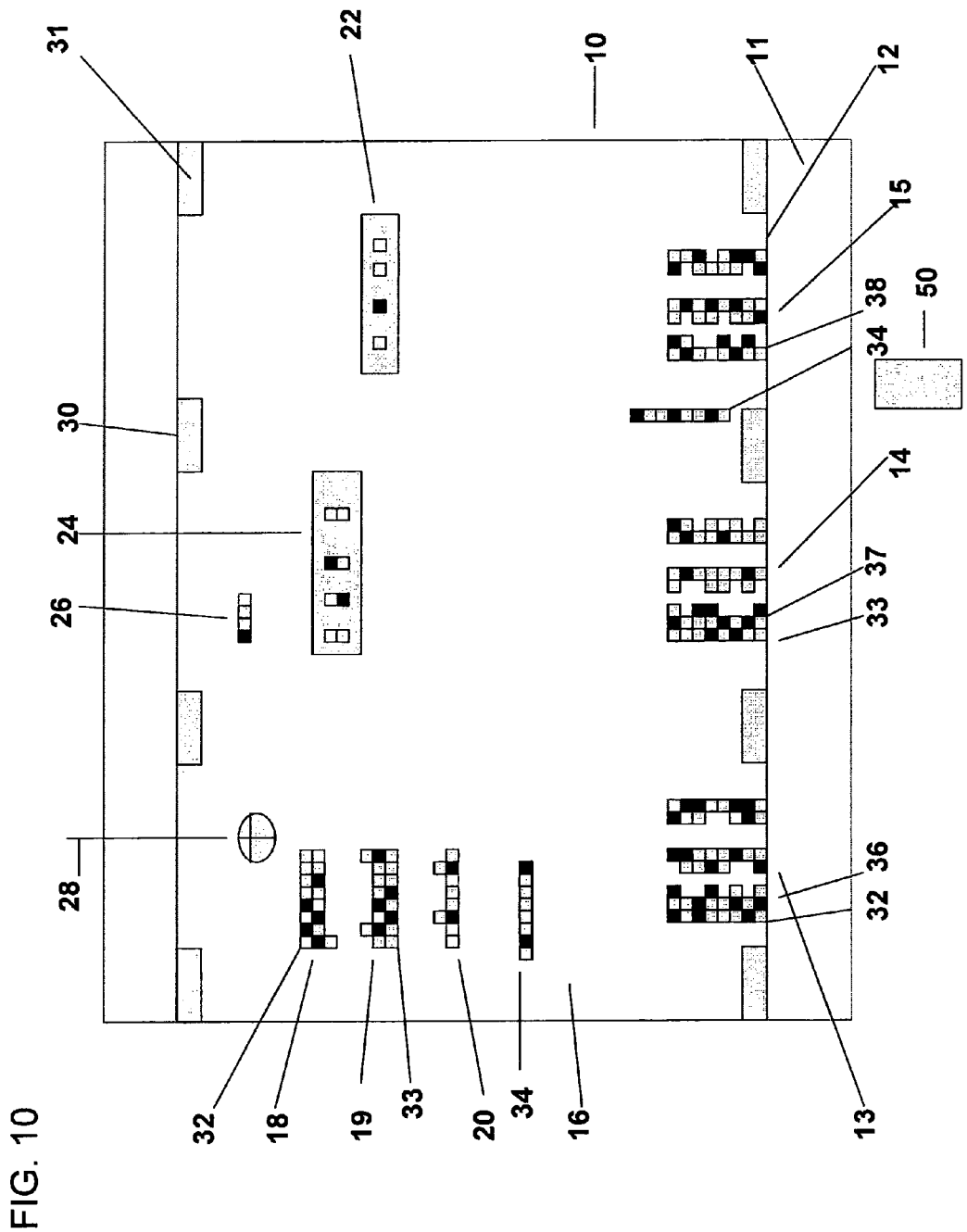
FIG. 10 illustrates a cross-sectional view of a reaction cartridge capable of evanescent wave detection of fluorescently tagged amplicons in a microarrayed PCR process at the denaturation stage of the PCR process for the third group of target nucleic acids probes.

FIG. 10 is a cross-sectional view of a reaction cartridge 10 capable of evanescent wave detection of fluorescently tagged amplicons in a microarrayed PCR process at the denaturation stage of the PCR process. In this stage, the mixture within the reaction cartridge 10 has been heated to close to 100° C., and optimally to about 94° C. At this temperature, the DNA is denatured, that is, it separates into individual, single strands. When cooled to the hybridization temperature ($T_{h3}$) for the third group of target nucleic acids probes 15 in the next stage of the PCR process, the third target nucleic acid strand 20 as well as each of the third fluorescently tagged amplicon 34 will anneal with fluorescently tagged primers 26. The annealed fluorescently tagged primers 26 will be extended as the thermostable DNA polymerase 28 adds appropriate nucleotides, until the third target nucleic acid strand 20 and the third fluorescently tagged amplicon 34 will be hybridized to a new amplicon, which is a copy or a complementary copy of the original third target nucleic acid strand 20. Amplification may also take place during the detection cycle. As such, the detection cycle is conducted by, for example, programming the number of amplification cycles before detection and the detection frequency (e.g., the number of amplification cycles between every detection cycle).

Figure 11:
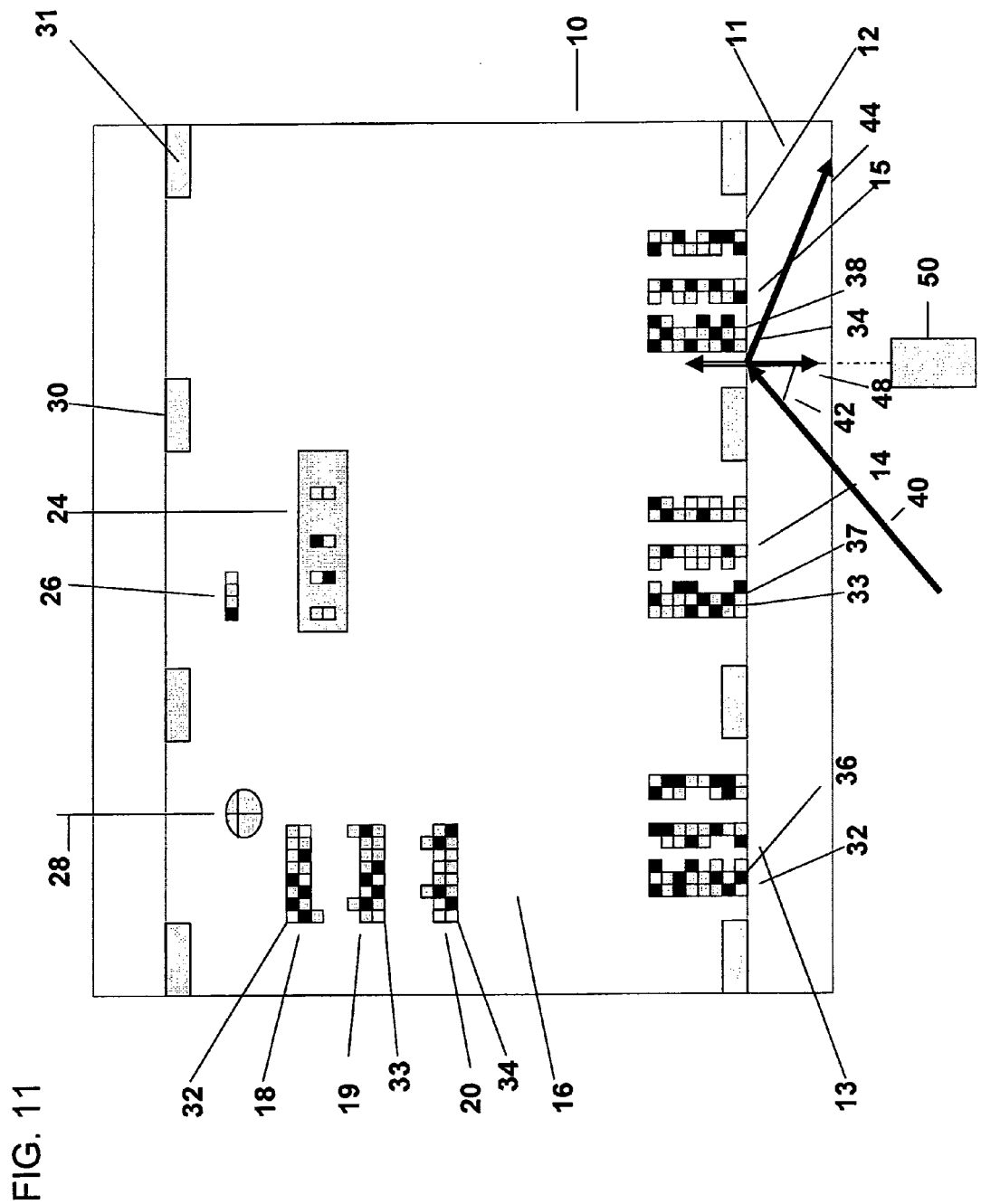
FIG. 11 illustrates a cross-sectional view of a reaction cartridge showing evanescent wave detection of fluorescently tagged amplicons in a microarrayed PCR process at the detection stage of the PCR process for the third group of target nucleic acids probes.

FIG. 11 is cross-sectional view of a reaction cartridge 10 showing evanescent wave detection of fluorescently tagged amplicons in a microarrayed PCR process at the detection stage of the PCR process for the third group of target nucleic acids probes 15, further including an incident beam of light 40, an angle of incidence 42, a reflected beam of light 44, an evanescent wave of light 46, a fluorescent beam of light 48 and a fluorescent light detector 50. The detection stage can be coincident with the annealing and/or extension stage.

The present invention also provides a kit for detecting two or more target nucleic acids from one or more pathogens. The kit may include at least one primer pair and an oligonucleotide microarray that may include two or more groups of target nucleic acid probes. Although the foregoing discussion has used DNA as a nucleic acid, it would be obvious to a person of reasonable skill in the art to apply the methods disclosed herein to other nucleic acids, including RNA sequences or combinations of RNA and DNA sequences.

It is to be understood that certain descriptions of the present invention have been simplified to illustrate only those elements and limitations that are relevant to a clear understanding of the present invention, while eliminating, for purposes of clarity, other elements. Those of ordinary skill in the art, upon considering the present description of the invention, will recognize that other elements and/or limitations may be desirable in order to implement the present invention. However, because such other elements and/or limitations may be readily ascertained by one of ordinary skill upon considering the present description of the invention, and are not necessary for a complete understanding of the present invention, a discussion of such elements and limitations is not provided herein.

EXAMPLES

The following Example is illustrative of the above invention. One skilled in the art will readily recognize that the techniques and reagents described in the Example suggest many other ways in which the present invention could be practiced. It should be understood that many variations and modifications may be made while remaining within the scope of the invention.

Example 1

This example illustrates the use of a programmable oligonucleotide microarray for the parallel detection of nine species of bacteria. A probe is designed for the specific sequence region of each species of bacteria listed in Table 1. These probes are designed with different length and guanosine and cytosine (GC) ratio. The melting temperature ($T_m$) and the theoretical hybridization temperature ($T_h$) is calculated for each probe. The probes are divided into three groups, with the corresponding hybridization temperatures ($T_h$) of 59, 69, and 63° C., respectively. The actual hybridization temperature ($T_h$) of each probe is verified by the hybridization kinetic analysis. The hybridization kinetic analysis is carried out in the following way.

First, each probe is synthesized and immobilized on the surface of a glass plate. The glass plate makes up the hybridization and detection component of the microarray reaction chamber. The immobilization is be done using an aspirate-dispensing arrayer with the concentration of 20 micromolar (μM) in an appropriate buffer to optimize the reaction between probes and functional molecules on the surface of glass. The glass is assembled with other chamber parts, such as a plastic cartridge, to form a complete microarray reaction chamber. The glass is treated to remove unbounded probes. The surfaces of the complete microarray reaction chamber undergo a passivating treatment to reduce non-specific binding.

Second, for each probe, the corresponding target molecules are prepared in two certain concentrations. One concentration of the target molecules is in the middle of the detection range and is used for the specific signal detection. The other concentration of the target molecules is at the high end of the detection range and is used for the non-specific signal detection. All these target molecules are fluorescently tagged amplicons prepared by conventional PCR.

Third, for each probe, the corresponding target molecules with a concentration in the middle of the detection range are added to test the specific hybridization signals at a series of hybridization temperatures ($T_h$). For each hybridization temperature ($T_h$), the specific hybridization signal is recorded at an appropriate time to afford a curve of specific hybridization signal versus hybridization temperature ($T_h$). The highest hybridization temperature ($T_h$) is usually achieved at very low temperature, such as $T_h<T_m-30$.

For each probe, eight different target molecules with large concentrations are added to test the non-specific hybridization signal at a series of hybridization temperatures ($T_h$). For each hybridization temperature ($T_h$), the non-specific hybridization signal is recorded at an appropriate time. By this way, eight curves of non-specific hybridization signals versus hybridization temperature are achieved. With decreasing temperature, the non-specific hybridization will increase. The non-specific binding reaction with other non-related target molecules, which are not included in the detection spectrum, can also be done in this way.

The proper hybridization temperature ($T_h$) for each probe is determined by the following guidelines. First, the specific hybridization signal should be high, such as greater than about 70% of the highest hybridization signal. Second, the non-specific hybridization signal should not be detectable. The optimal hybridization temperature ($T_h$) of each probe should be is verified and adjusted, if needed. If the actual hybridization temperature ($T_h$) is similar to the theoretical hybridization temperature ($T_h$), the probe can be divided into three groups, as discussed above. Consequently, all these probes together with one or more optional internal control probes can be immobilized on a functional surface of a glass to form the reaction chamber, which can be used directly for detection. The probes are arrayed in groups, for example, the probes of the same group are spotted in the same line.

The reaction chamber can be used for the detection of the presence and its concentration of an arbitrary species of bacteria. For calibration purposes, a known concentration of one or more optional internal control target molecules may be added to the sample for testing.

A programmable detection file used in the detection system may be used to increase the detection efficiency. By using this program, the detection may be carried out at the end of an appropriate number of amplification cycles. The temperature of the chamber and the reagent inside will be elevated to about 90° C. and be kept for several seconds. At this temperature, the nucleic acid molecules will denature into single strands. The temperature is cooled down to hybridization temperature ($T_{h1}$), which is the average hybridization temperature ($T_h$) of the probe group 1 and has the highest hybridization temperature ($T_h$). At this temperature, target probes in group 1 will reach their optimal hybridization temperature ($T_{h1}$).

The laser, which is used to activate the fluorescent molecules near the hybridization site, is moved to the corresponding position. At this position, the incidence of the laser beam can activate the fluorescent molecules of probe group 1, while can not activate the fluorescent molecules in the other groups of probes. As a result, only the hybridization signal of probe group 1 is detected and recorded.

Subsequently, the temperature is decreased to hybridization temperature ($T_{h2}$), which is the average hybridization temperature of probe group 2 and has a hybridization temperature ($T_h$) in the middle of the temperature range. At this temperature, target probes in group 2 will reach their optimal hybridization temperature ($T_{h2}$).

The laser, which is used to activate the fluorescent molecules near the hybridization site, is moved to the corresponding position. At this position, the incidence of the laser beam can activate the fluorescent molecules of probe group 2, while can not activate the fluorescent molecules in the other groups of probes. As a result, only the hybridization signal of probe group 2 is detected and recorded.

Subsequently, the temperature is decreased to hybridization temperature ($T_{h3}$), which is the average hybridization temperature of probe group 3 and has a hybridization temperature ($T_h$) at the low end of the temperature range. At this temperature, target probes in group 3 will reach their optimal hybridization temperature ($T_{h3}$).

The laser, which is used to activate the fluorescent molecules near the hybridization site, is moved to the corresponding position. At this position, the incidence of the laser beam can activate the fluorescent molecules of probe group 3, while can not activate the fluorescent molecules in the other groups of probes. As a result, only the hybridization signal of probe group 3 is detected and recorded.

Subsequently, the temperature is decreased to the hybridization temperature ($T_{hc}$) of the one of the optional internal control probes. In this example, $T_{hc}<T_{h3}<T_{h2}<T_{h1}$. However, other various combinations are also possible including, for example, $T_{h3}<T_{hc}<T_{h2}<T_{h1}$, $T_{h3}<T_{h2}<T_{hc}<T_{h1}$, and $T_{h3}<T_{h2}<T_{h1}<T_{hc}$. At hybridization temperature ($T_{hc}$), the internal control probes will reach their optimal hybridization temperature.

The laser, which is used to activate the fluorescent molecules near the hybridization site, is moved to the corresponding position. At this position, the incidence of the laser beam can activate the fluorescent molecules of one of the optional internal control probe groups, while can not activate the fluorescent molecules in the other groups of probes. As a result, only the hybridization signal of one of the optional internal control probe groups is detected and recorded.

In this example, one of the optional internal control probes is used. However, two or more optional internal control probes may be used and their corresponding hybridization temperatures may range from below $T_{h3}$ to above $T_{h1}$.

This detection process may be done in a circular mode. For example, the detection may be done every three amplification cycles until the hybridization signal of the suspected target molecule reaches a threshold. The CT number is the number of amplification cycles for the suspected target molecule to reach its threshold. By comparing the CT of the suspected target molecule and the CT of the internal control molecules with the standard curve of the suspected target molecule and the calibration curves (the standard curve of the internal control target molecules), the actual concentration of the suspected target molecules may be inferred.

For example, the CT number of a suspected target molecule may indicate that the concentration of the suspected target molecule is about 10000 copies/ml. At the same time, the calibration curve may reveal that the concentration of the optional internal control target is estimated to be low, for example, by about ten fold. Therefore, the actual concentration of the suspected target molecule would be about 100,000 copies/ml.

The invention has been described with reference to various specific embodiments and techniques. However, it should be understood that many variations and modifications may be made while remaining within the spirit and scope of the invention.

What is claimed is:

1. A quantitative method for analyzing target nucleic acids, comprising
    obtaining a substrate with three or more groups of different target nucleic acid probes immobilized in independent lines on an upper surface of the substrate, wherein each group has three or more probes, the probes within each group are different from probes in other groups, and the probe groups are arrayed on the substrate in order of decreasing hybridization temperature, but probes within each line have optimal hybridization temperatures within five percent of each other;
    annealing one or more fluorescently tagged target amplicons to target nucleic acid probes;
    independently and sequentially activating a fluorescence response from fluorescently tagged target amplicons hybridized to each line of target nucleic acid probes at the hybridization temperature of each group;
    independently and sequentially detecting each fluorescence response for a quantitative analysis of one or more target nucleic acids at the hybridization temperature of each line of target nucleic acid probes;
    wherein the activating of the each fluorescence response is by using an evanescent wave of a predetermined wavelength.

2. The quantitative method of claim 1, wherein the hybridization temperature of probes in each line is the average of the hybridization temperatures of the one or more target nucleic acid probes in each line.

3. The quantitative method of claim 1, wherein the annealing occurs during a polymerase chain reaction.

4. The quantitative method of claim 3, wherein the detecting of each fluorescence response occurs during the annealing step or an extending step of the polymerase chain reaction.

5. The quantitative method of claim 4, wherein polymerase chain reaction is a real-time polymerase chain reaction.

6. The quantitative method of claim 1, wherein the substrate comprises a material selected from a silicon, a plastic, a glass, a quartz glass, a ceramic, a rubber, a metal, a polymer, a hybridization membrane, or a combination thereof.

7. The quantitative method of claim 1, wherein the one or more target nucleic acid probes are printed and immobilized onto a substrate using a micro-array printer.

8. The quantitative method of claim 7, wherein the substrate is chemically modified with a reagent selected from a silane, avidin, poly-L-lysine, streptavidin, a polysaccharide, a mercaptan, or a combination thereof.

9. The quantitative method of claim 1, wherein each line of target nucleic acid probes comprises one or more groups of target nucleic acid probes.

10. The quantitative method of claim 1, wherein the one or more target nucleic acids are derived from one or more pathogens, wherein the one or more pathogens is a virus, a bacterium, an archaea, a fungus, a protozoan, a mycoplasma, a prion, a parasitic organism, or combinations thereof.

11. The quantitative method of claim 10, wherein the one or more pathogens is *Rickettsia, Chlamydia, Mycoplasma, Spirochete, Streptococcus, Staphylococcus, L. monocytogenes, N meningitides, E. coli, H. influenzae, B. burgdorferi, Leptospira, Proteus, Anaerobacter, Salmonella, M. tuberculosis, Enterococcus, Poliovirus, Enterovirus, Coxsackievirus,* HSV-1, HSV-2, or combinations thereof.

* * * * *